United States Patent
Dijksman et al.

(10) Patent No.: US 8,911,425 B2
(45) Date of Patent: Dec. 16, 2014

(54) ELECTRONIC PILL COMPRISING A MEDICINE RESERVOIR

(75) Inventors: Johan Frederik Dijksman, Eindhoven (NL); Anke Pierik, Eindhoven (NL); Jeff Shimizu, Cortlandt Manor, NY (US); Hans Zou, Windsor, NY (US)

(73) Assignee: Medimetrics Personalized Drug Delivery, Eindhoven (NL)

( * ) Notice: Subject to any disclaimer, the term of this patent is extended or adjusted under 35 U.S.C. 154(b) by 452 days.

(21) Appl. No.: 12/995,817

(22) PCT Filed: Jul. 3, 2009

(86) PCT No.: PCT/IB2009/052894
§ 371 (c)(1),
(2), (4) Date: Jan. 6, 2011

(87) PCT Pub. No.: WO2010/004490
PCT Pub. Date: Jan. 14, 2010

(65) Prior Publication Data
US 2011/0106063 A1    May 5, 2011

Related U.S. Application Data

(66) Substitute for application No. 61/078,469, filed on Jul. 7, 2008.

(51) Int. Cl.
| | |
|---|---|
| A61K 9/22 | (2006.01) |
| A61K 47/00 | (2006.01) |
| A61K 9/00 | (2006.01) |
| A61K 9/48 | (2006.01) |
| A61M 31/00 | (2006.01) |

(52) U.S. Cl.
CPC .............. *A61K 9/4808* (2013.01); *A61K 47/00* (2013.01); *A61K 9/0009* (2013.01); *A61M 31/002* (2013.01)

USPC .......... 604/890.1; 604/57; 604/58; 604/891.1

(58) Field of Classification Search
USPC ................ 604/890.1, 57, 58, 60, 502, 891.1, 604/93.01, 288.04
See application file for complete search history.

(56) References Cited

U.S. PATENT DOCUMENTS

| | | |
|---|---|---|
| 5,098,425 A | 3/1992 | Eckenhoff |
| 2004/0077604 A1 | 4/2004 | Lichtenberger |

(Continued)

FOREIGN PATENT DOCUMENTS

| | | |
|---|---|---|
| JP | 2006517827 | 8/2006 |
| JP | 2007312850 | 12/2007 |

(Continued)

OTHER PUBLICATIONS

The Chinese Office Action mailed Jul. 1, 2013 for Rusian patent application No. 200980126435.8, a counterpart foreign application of U.S. Appl. No. 12/995,817, 12 pages.

(Continued)

*Primary Examiner* — Kevin C Sirmons
*Assistant Examiner* — Deanna K Hall
(74) *Attorney, Agent, or Firm* — Lee & Hayes, PLLC

(57) ABSTRACT

Electronic pill (1, 11) comprising at least one medicine reservoir (2, 12) with a solid powder or granulate medicine, a discharge opening (3, 13) and an actuator responsive to control circuitry for displacing medicine from the reservoir (2, 12) to the discharge opening (3, 13). The medicine comprises a dispersion of one or more active ingredients—e.g., solids in powder or granulate form—in an inert carrier matrix. Optionally, the active ingredients are dispersed using intestinal moisture absorbed into the pill via a semi-permeable wall section (14).

10 Claims, 2 Drawing Sheets

(56) References Cited

U.S. PATENT DOCUMENTS

| | | | |
|---|---|---|---|
| 2004/0253304 A1* | 12/2004 | Gross et al. | 424/451 |
| 2008/0051635 A1 | 2/2008 | Tanaka et al. | |

FOREIGN PATENT DOCUMENTS

| | | |
|---|---|---|
| JP | 2009541298 | 11/2009 |
| JP | 2010504135 | 2/2010 |
| WO | WO0145789 | 6/2001 |
| WO | WO2004066903 | 8/2004 |
| WO | WO2004096176 | 11/2004 |
| WO | WO2006077529 | 7/2006 |
| WO | WO2007056529 | 5/2007 |
| WO | WO2007103547 | 9/2007 |
| WO | WO2007148238 | 12/2007 |
| WO | WO2008038199 | 4/2008 |

OTHER PUBLICATIONS

The Japanese Office Action mailed Sep. 17, 2013 for Japanese patent application No. 2011517290, a counterpart foreign application of U.S. Appl. No. 12/995,817, 8 pages.

* cited by examiner

ELECTRONIC PILL COMPRISING A MEDICINE RESERVOIR

CROSS REFERENCE TO RELATED CASES

Applicants claim the benefit of International Application Number PCT/IB2009/052894, filed Jul. 3, 2009, and Provisional Application Ser. No. 61/078,469, filed Jul. 7, 2008.

FIELD OF THE INVENTION

The present invention relates to an electronic pill for dosing a medicine in a controlled way, while passing the gastrointestinal tract. The invention also relates to a method for preparing an electronic pill.

BACKGROUND OF THE INVENTION

Electronic pills are ingestible capsules with electronic control circuitry to dispense medicine for therapeutic treatment during traversal of the alimentary tract. An electronic pill generally comprises a medicine reservoir, a dispensing opening, and a pump for transporting the medicine from the reservoir to the dispensing opening. Generally, the electronic pill also comprises control means to activate the dispensing pump at the desired moment, e.g. responsive to a signal from a sensor, such as a pH sensor which can be an integral part of the pill. After swallowing the pill is moved along the alimentary tract by the peristaltic movement of the muscles along the alimentary tract. During its travel through the intestines the pill drifts from the pylorus to the ileocaecal valve at about 1 m/hour. Due to the peristalsis of the small intestines superposed on the drift velocity, large velocity variations occur pushing the pill back and forth through the intestines. This way medication released from the pill is mixed thoroughly before it will be taken up through the wall of the intestines or becomes locally effective.

An example of an electronic pill is disclosed in WO 2006077529.

Hitherto, electronic pills are particularly suitable for dispensing liquid medicines. However, many medicines are in powder form. Medicines in powder form generally have better stability and shelf life. The problem is that dry powder exhibits elastic and plastic and viscous behavior. It is basically the mechanical strength of the particles that count. When tightly packed it behaves like an elastic body, requiring large mechanical loads to get it deformed. When the interactions between the particles of the powder are weaker than the mechanical strength of the powder particles, the packed powder behaves like an elastic plastic material. Under a certain value of the mechanical load the powder behaves like an elastic body, above that value it shows plastic behavior. When strongly agitated it acts like a fluid: the space between the particles of the powder are occupied by air or liquid and this causes that the powder particles can be easily displaced at low mechanical load. Due to this complex behavior of powders accurate metering and dispensing in miniature systems, such as electronic pills, is problematic.

SUMMARY OF THE INVENTION

It is an object of the present invention to provide an electronic pill system which allows accurate metering and dosing of medicines, even when these are available in powder-form.

The object of the invention is achieved with an electronic pill according to the invention, wherein the pill comprises at least one medicine reservoir with a discharge opening and at least partly filled with a medicine comprising a dispersion of one or more active ingredients in an inert carrier. In this respect inert means that the carrier material is not chemically reactive with the active ingredient and the gastrointestinal tissue of the patient and that it does not dissolve the ingredient.

After swallowing the electronic pill by a patient, the medicinal composition is dispensed on command. Due to the peristalsis of the intestines, the inert carrier is washed away and the powder is exposed to the aqueous environment of the intestinal interior. The medicine dissolves and passes the intestinal barrier or becomes locally active.

The pharmaceutically active ingredient can for example be a solid powder material. The average particle size of the powder particles in the pasty dispersion can for example be less than or equal to 10 µm, for instance 50 nm-10 µm or 50 nm-5 µm or 50 nm-1 µm. Micro-spheres with an average particle size of 50 nm-5 µm, e.g., of 50 nm-4 µm, or 50 nm-2 µm, are suitable examples.

In comparison with direct administration of a medicine in powder form, the use of an electronic pill has the additional advantage that the medicine is effectively protected against enzymatic breakdown in the mouth and chemical breakdown in the stomach.

The lower the content of powder in the dispersion the smaller the interaction between the particles and the easier the paste can be deformed.

The dispersion can for example be a paste. Compositions having a viscosity of below 4 Pa·s, e.g., of 0.1-2 Pa·s measured at 20° C. and at a shear rate of 104 s−1 are considered to be pastes or pasty dispersions particularly suitable for dispensing by an electronic pill. A suitable way to measure fixed shear-rate viscosity is the cone and plate technique described in ASTM Test D4287-87, used in the oscillatory mode, with a shear rate of 104 s−1. The cone may, e.g., have an angle of 0.5° and a radius of 7.5 mm.

A pasty dispersion or paste is a substance that behaves as a solid until a sufficiently large load or stress is applied, at which point it flows like a fluid.

The active ingredient can for example be a pharmaceutically active ingredient or mixture or a nutrient or nutrient mixture, optionally with dispersants, additives and auxiliary agents.

An inert carrier matrix is a compound or composition of compounds which are not chemically active with the active ingredients and which do not dissolve the powder particles.

The carrier material should be safe and biocompatible for the patients health if absorbed by the body. Oils used in food technology such as olive oil or sunflower oil, are safe examples. Some carriers are not food based, but have been proven safe even if they are absorbed by the body such as glycerol, polyethylene glycol of any suitable molecular weight (e.g. PEG 200, PEG 400 or PEG 600). Another group of suitable carriers are those which are absorbed by the body only to a very little extent and can pass through the gastrointestinal tract unchanged, such as mineral oil and polymers, for example, carbomer. They are considered safe and biocompatible because they do not interact with the human biological system, so there is no long-term small dose effect.

The inert carrier can for example be a fatty compound such as a fatty alcohol, a fatty acid ester or an oil, such as the above mentioned oils, or mixtures thereof. Further suitable oils are any oil approved for human or animal consumption by the FDA and/or EMEA including natural oils such as plant or animal oils or their derivatives or synthetic oils and especially natural oil that are rich in phospholipids such as lecithin oils from soy beans. Exemplary examples of such oils include essential oils, vegetable oils and hydrogenated vegetable oils, animal oils such as peanut oil, canola oil, avocado oil, safflower oil, olive oil, corn oil, soy bean oil, sesame oil, vitamin A, vitamin D, vitamin E, fish oils, or the like.

The inert carrier can also be an ointment. An ointment is a viscous semi-solid compound. The ointment can be a hydrocarbon base, e.g., hard or soft paraffin; absorption base, e.g. wool fat or beewax; or water soluble base, e.g., macrogols 200, 300, 400.

A further suitable carrier is water. Optionally, water from the intestinal environment can be used. To that end, the electronic pill can have a medicine reservoir with a semi-permeable membrane. Suitable semi-permeable are for example cellulose acetates and cellulose alkanyates or alkenylates.

Examples of medicines that can be administered this way, are aminosalicylates and corticosteroids, such as budesonide, a tasteless powder which is practically insoluble in water and which is chemically defined as (RS)-11b, 16 a, 17, 21-tetrahydroxypregna-1,4-diene-3,20-dione cyclic 16,17-acetal with butyraldehyde. It can for example be used to treat Crohn's disease. A suitable matrix carrier material for this drug is ethyl cellulose which dissolves in intestinal moisture thereby releasing the medicine powder.

To prevent sticking of the powder dispersion to the exterior of the electronic pill after discharge, the pill can be coated with a non-stick coating, e.g. of a fluoropolymer such as polytetrafluoroethylene, such as Teflon® ex DuPont.

Optionally, the electronically controlled pill or medicine delivery system can comprise electronic circuitry programmed or controlled to deliver or dispense a medicine according to a dispensing timing pattern while traversing through the gastrointestinal tract. The dispensing timing pattern can be preset and it can be fixed not being susceptible to a person's physiological processes and conditions, mood, earlier-administered medicines, etc. The electronically controlled pill can include control and timing circuitry for controlling the opening and closing of a valve or hatch according to the desired dispensing timing pattern for dispensing a medicine stored within a medicine reservoir of the pill. The electronically controlled pill allows a person to take all pills substantially simultaneously, e.g. with breakfast, so that no more pills are required for the day. Medication that does not fit into one electronically controlled pill can be coordinated with other electronically controlled pills for the full day's payload regimen.

The dispensing pattern can be varied from person to person depending on each person's physical condition, age, gender, ailments, etc. Further, at a preset moment in time during the dispensing timing patterns, the electronically controlled pills present in the body may be programmed to stop dispensing medicine, in the expectation that a new set of pills will be taken. This prevents accidental overdose by having only the most recently taken pills dispensing medicine in the body.

The electronic pill according to the invention can be used for human or animal patients. In order to be swallowable for human patients, the pill can for example be mainly cylindrical having a length of 2-3 cm or less and a diameter of about 1 cm or less.

BRIEF DESCRIPTION OF THE DRAWINGS

The present invention will be elucidated with reference to the figures wherein.

DETAILED DESCRIPTION OF EMBODIMENTS

Figure 1:
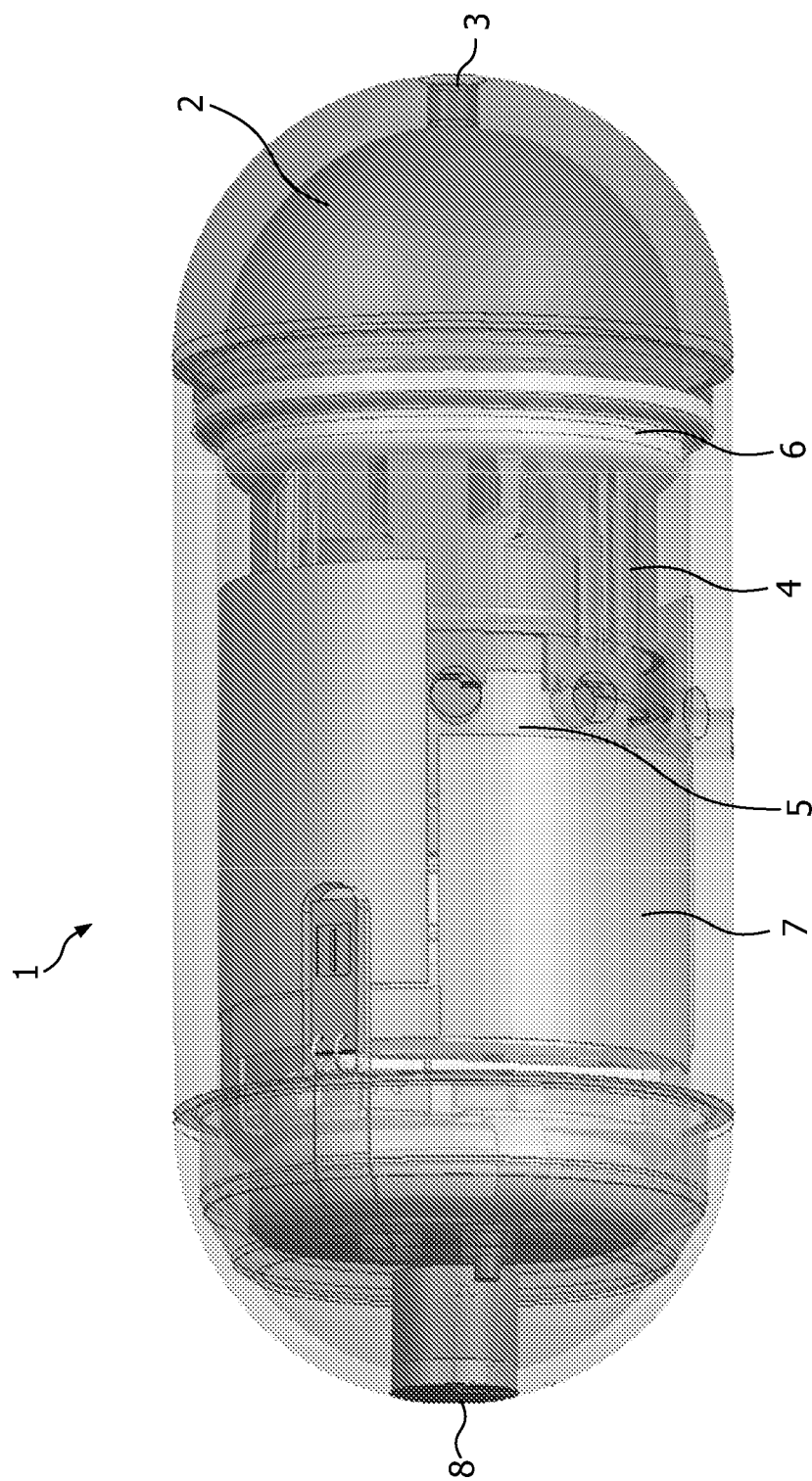
FIG. 1: shows in perspective transparent view an electronically controllable pill according to the present invention.

FIG. 1 shows an electronically controllable pill 1 comprising a medicine reservoir 2 with a discharge opening 3. The medicine reservoir is pre-fillable with a pasty composition comprising a medicine in powder form dispersed in an inert carrier. The pre-dispersed composition is inserted into the medicine reservoir, e.g. by using a syringe. A piston 4 can be activated by a miniature electrical motor 5 to discharge the paste. The medicine reservoir 2 is sealed against the piston by a rolling sock seal 6. The motor 5 is powered by a battery 7. The pill further comprises a sensor 8, e.g. a pH sensor or any other suitable sensor to determine the location of the pill 1 within the gastro-intestinal tract. Electronic circuitry within the electronic pill 1 activates the motor 5 responsive to a signal from the sensor 8. Alternatively or additionally, the pill 1 can comprise means for wireless communication with a terminal outside the patient, so the passage for the pill through the gastro-intestinal tract and the dosing of medicine can be monitored and/or controlled by a medical doctor or assistant.

Figure 2:
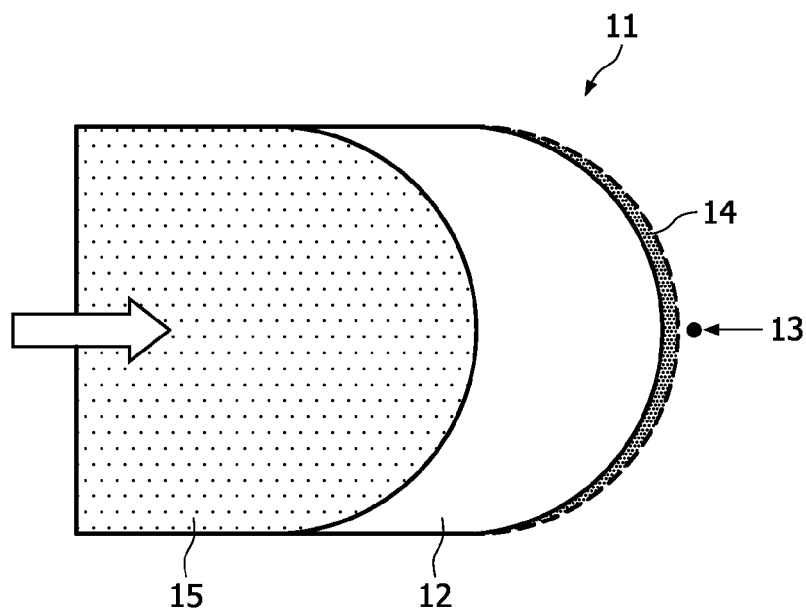
FIG. 2: shows schematically an alternative embodiment of an electronically controlled pill according to the invention.

FIG. 2 shows an alternative embodiment of an electronic pill 11 with a medicine reservoir 12 pre-fillable with a dry solid powder medicine, which may be poorly soluble in water. The medicine reservoir 12 comprises a discharge opening 13 and is bordered by an exterior wall 14 formed by a semi-permeable material. Upon arrival in the gastrointestinal tract intestinal moisture is absorbed via the semi-permeable membrane 14. The membrane 14 is located primarily at the discharge opening 13. After the electronic pill 11 is swallowed water is drawn in through the membrane and mixes with the powder material in the reservoir. The mixture will have the highest water content near the membrane 14 and the discharge opening 13, so it will flow most easily near the discharge opening 13. A driving force for pushing out the slurried medicinal powder via the discharge opening 13 is provided by a mechanical actuator and piston 15 controlled in the same way as set out above for the embodiment of FIG. 1. The displacement of the piston can be measured so the amount of actually delivered medicine can accurately be monitored. To limit diffusion of the material, especially while in the stomach, the discharge opening may be provided with a one-way valve or a plug that either dissolves or is expelled at the beginning of the intended delivery profile.

Figure 3A:
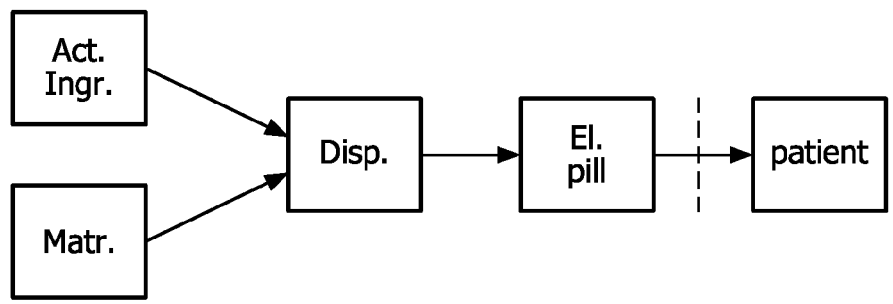
FIG. 3: shows a flow chart representing a first embodiment of the method according to the present invention.

FIG. 3A shows a flow chart representing a first embodiment of the method according to the invention. A pharmaceutically active ingredient in powder form is dispersed into a matrix carrier to form a dispersion, e.g., a pasty dispersion. An electronic pill comprising a medicine reservoir, as described above, is then filled with the dispersion. After that, the electronic pill can be used and swallowed by a patient for targeted medicine delivery in the gastrointestinal tract.

Figure 3B:
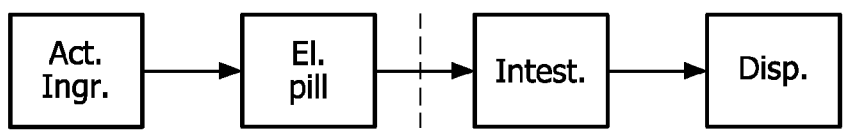

FIG. 3B represents an alternative embodiment of the method according to the invention. A pharmaceutically active ingredient in dry powder form is inserted in an electronic pill having a medicine reservoir with a semi-permeable wall, as is for instance described above under reference to FIG. 2. After arrival in the patient's intestines, intestinal moisture enters the medicine reservoir via the semi-permeable wall and disperses the active ingredient. The thus obtained dispersion is subsequently dispensed at a targeted part of the patient gastrointestinal tract.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An electronic pill comprising:
at least one medicine reservoir at least partly filled with a medicine;
at least one discharge opening; and
an actuator responsive to control circuitry for displacing medicine from the reservoir to the discharge opening, wherein the medicine comprises a dispersion of one or more active ingredients in a liquid inert carrier matrix and wherein the medicine is present in the reservoir at the time of administration of the electronic pill.

2. The electronic pill according to claim 1 wherein at least a part of the one or more active ingredients is a solid powder material.

3. The electronic pill according to claim 1 wherein the inert carrier matrix comprises at least one compound selected from the group of oils and ointments.

4. The electronic pill according to claim 1 wherein the dispersion has a viscosity of 0.1- 2 Pa·s measured at 20° C. with a shear rate of 104/s.

5. The electronic pill according to claim 1 wherein the electronic pill has a housing coated with a non-stick coating.

6. The electronic pill according to claim 5 wherein the non-stick coating comprises one or more fluoropolymer binders.

7. The electronic pill according to claim 1, wherein the medicine is a pasty dispersion.

8. An electronic pill comprising:
a reservoir defined by a sidewall of the electronic pill and a seal inside the pill,
a discharge opening in the sidewall defining the reservoir;
an actuator responsive to control circuitry for displacing a product from the reservoir through the discharge opening; and
a semi-permeable membrane forming a portion of the sidewall at the discharge opening, the remainder of the sidewall defining the reservoir being impermeable, the semi-permeable membrane allowing fluid into the reservoir only adjacent the discharge opening, to mix with the product to form a mixture having a relatively higher water content proximate the discharge opening.

9. The electronic pill according to claim 8, wherein the product is a powder.

10. The electronic pill according to claim 8, wherein the mixture having the relatively higher water content proximate the discharge opening flows more easily at the discharge opening.

* * * * *